United States Patent
Gratz et al.

(10) Patent No.: US 9,452,243 B2
(45) Date of Patent: Sep. 27, 2016

(54) IMPLANT COMPRISING AN ACTIVE-AGENT-CONTAINING COATING COVERING THE IMPLANT AT LEAST IN SECTIONS

(75) Inventors: Matthias Gratz, Erlangen (DE);
Alexander Borck, Aurachtal (DE);
Alexander Rzany, Nuremberg (DE);
Robert Schmiedl, Hirschaid (DE);
Matthias Fringes, Ansbach (DE);
Claus Harder, Uttenreuth (DE)

(73) Assignee: BIOTRONIK AG, Buelach (CH)

( * ) Notice: Subject to any disclaimer, the term of this patent is extended or adjusted under 35 U.S.C. 154(b) by 561 days.

(21) Appl. No.: 13/306,238

(22) Filed: Nov. 29, 2011

(65) Prior Publication Data
US 2012/0150284 A1 Jun. 14, 2012

Related U.S. Application Data

(60) Provisional application No. 61/420,805, filed on Dec. 8, 2010.

(51) Int. Cl.
| | | |
|---|---|---|
| *A61F 2/82* | (2013.01) | |
| *A61L 31/16* | (2006.01) | |
| *A61L 31/02* | (2006.01) | |
| *A61L 31/08* | (2006.01) | |
| *A61L 31/14* | (2006.01) | |

(52) U.S. Cl.
CPC .............. *A61L 31/16* (2013.01); *A61L 31/022* (2013.01); *A61L 31/08* (2013.01); *A61L 31/148* (2013.01)

(58) Field of Classification Search
CPC .......................................................... A61F 2/82
USPC ................................................ 623/1.42–1.46
See application file for complete search history.

(56) References Cited

U.S. PATENT DOCUMENTS

| | | | |
|---|---|---|---|
| 8,257,729 B2 | 9/2012 | Schmitz et al. | |
| 2004/0034409 A1* | 2/2004 | Heublein et al. | 623/1.46 |
| 2006/0155370 A1* | 7/2006 | Brister | 623/1.46 |
| 2007/0207186 A1* | 9/2007 | Scanlon et al. | 424/424 |
| 2007/0244548 A1 | 10/2007 | Myers et al. | |
| 2008/0082162 A1* | 4/2008 | Boismier | A61F 2/91 |
| | | | 623/1.38 |
| 2009/0024200 A1 | 1/2009 | Wilcox et al. | |

FOREIGN PATENT DOCUMENTS

EP 2070558 A2 6/2009

OTHER PUBLICATIONS

EP11189695.7 European Search Report mailed Aug. 28, 2014.

* cited by examiner

*Primary Examiner* — Matthew Schall
(74) *Attorney, Agent, or Firm* — Wagenknecht IP Law Group PC

(57) ABSTRACT

The invention relates to an implant comprising an active-agent-containing coating which covers the implant at least in sections. The coating is composed of at least two subsections; a first subsection contains the at least one active substance, and a second subsection contains an auxiliary agent.

16 Claims, 1 Drawing Sheet

IMPLANT COMPRISING AN ACTIVE-AGENT-CONTAINING COATING COVERING THE IMPLANT AT LEAST IN SECTIONS

CROSS REFERENCE TO RELATED APPLICATIONS

This invention claims benefit of priority to U.S. patent application Ser. No. 61/420,805, filed Dec. 8, 2010; the content of which is herein incorporated by reference in its entirety.

TECHNICAL FIELD

The invention relates to an implant comprising an active-agent-containing coating which covers the implant at least in sections.

BACKGROUND

Implants are utilized in modern medical technology in a variety of embodiments. They are used e.g. to support vessels, hollow organs, and ductal systems (endovascular implants e.g. stents), to attach and temporarily fix tissue implants and tissue transplants in position, and for orthopedic purposes such as pins, plates, or screws. The stent is a form of an implant that is used particularly frequently.

Stent implantation has become established as one of the most effective therapeutic measures for treating vascular disease. Stents are used to provide support in a patient's hollow organs. For this purpose, stents of a conventional design have a filigree support structure composed of metallic struts; the support structure is initially provided in a compressed form for insertion into the body, and is expanded at the application site. One of the main applications of stents of this type is to permanently or temporarily widen and hold open vasoconstrictions, in particular constrictions (stenoses) of the coronary arteries. In addition, aneurysm stents are known, for example, which are used primarily to seal the aneuryism. They also perform the support function.

Stents include a circumferential wall having a support force that suffices to hold the constricted vessel open to the desired extent; stents also include a tubular base body through which blood continues to flow without restriction. The circumferential wall is typically formed by a latticed support structure that enables the stent to be inserted, in a compressed state having a small outer diameter, until it reaches the constriction in the particular vessel to be treated, and to be expanded there, e.g. using a balloon catheter, until the vessel finally has the desired, enlarged inner diameter. Alternatively, materials having a memory effect, such as Nitinol, are capable of self-expansion in the absence of a restoring force that holds the implant at a small diameter. The restoring force is typically exerted on the material by a protective tube.

The implant, in particular the stent, has a base body composed of an implant material. An implant material is a nonliving material that is used for a medical application and interacts with biological systems. A prerequisite for the use of a material as an implant material that is comes in contact with the physical surroundings when used as intended is its biocompatibility. "Biocompatibility" refers to the capability of a material to evoke an appropriate tissue response in a specific application. This includes an adaptation of the chemical, physical, biological, and morphological surface properties of an implant to the recipient tissue, with the objective of achieving a clinically desired interaction. The biocompatibility of the implant material is furthermore dependent on the time sequence of the response of the biosystem in which the implant is placed. For example, irritations and inflammations, which can cause tissue changes, occur over the relative short term. Biological systems therefore respond differently depending on the properties of the implant material. Depending on the response of the biosystem, implant materials can be subdivided into bioactive, bioinert, and degradable/resorbable (referred to here as biocorrodible) materials.

Implant materials include polymers, metallic materials, and ceramic materials (as a coating, for example). Biocompatible metals and metal alloys for permanent implants contain e.g. stainless steels (e.g. 316L), cobalt-based alloys (e.g. CoCrMo casting alloys, CoCrMo forging alloys, CoCrWNi forging alloys, and CoCrNiMo forging alloys), pure titanium and titanium alloys (e.g. CP titanium, TiAl6V4 or TiAl6Nb7), nickel-titanium alloys (e.g. NiTiNo1), and gold alloys. In the field of biocorrodible stents, the use of magnesium or pure iron and biocorrodible base alloys of the elements magnesium, iron, zinc, molybdenum, and tungsten is proposed.

It is known that a greater level of biocompatibility can be achieved by coating implant materials with particularly tissue-compatible materials. These materials are usually organic or synthetic-polymeric in nature and are partially of natural origin. Further strategies for preventing restenosis focus on inhibiting proliferation using medication e.g. treatment using cytostatic agents. The active agents can be provided e.g. on the implant surface in the form of a coating that releases an active agent.

The active agents are applied directly as a coating or are embedded in an elution matrix. In the case of implants composed of biocorrodible materials in particular, it should also be possible for the elution matrix to be degraded in vivo. The disadvantage of degradable and permanent polymers, which are typically used in active-agent-eluting implants as an elution matrix, is that they induce inflammatory responses at the implantation site over the long-term, thereby affecting the clinical result. A polymer-based elution matrix should therefore be eliminated if possible.

Implants without a polymer-based elution matrix are basically known from the prior art. The substance, which usually has an antiproliferative effect, can be applied in pure form or in a mixture with an excipient (auxiliary agent as the carrier) directly to the surface of the implant which can be smooth, roughened, or provided with structural recesses and which are used as a reservoir.

Such implants have the disadvantage, however, that adhesion to the vascular wall is delayed, or occurs only partially or not at all over the long term. The risk therefore results e.g. of stent thrombosis occurring over the long term; to prevent this, systematic anticoagulation therapy is applied in clinical practice. This "dual antiplatelet therapy" (DAPT) has numerous clinical disadvantages that ultimately must be put up with in the form of delayed (or the absence of) adhesion of conventional implants.

SUMMARY

One or more of the aforementioned disadvantages of the prior art are overcome or at least diminished by the use of the implant according to the invention. The implant comprises an active-agent-containing coating which covers the implant at least in sections. The coating is composed of at least two subsections; a first subsection contains the at least one active substance, and a second subsection contains an auxiliary agent.

The invention is based on the finding that a polymeric elution matrix can be omitted if, instead, the active agent is applied in a structured manner, wherein the sections of the coating not coated with the active agent are covered by an auxiliary agent. The sections of the implant surfaces covered by the auxiliary agent and the active agent therefore form a closed surface. The auxiliary agent is designed such that it dissolves immediately after implantation. As a result, the structured active-agent sections are exposed, and the surfaces of these sections can be enlarged greatly toward the surrounding medium, thereby also making it possible to improve an initial elution characteristic of the active agent. However, the auxiliary agent is still present during implantation, thereby protecting the structure against wear and/or being washed away while it is being advanced toward the implantation site and while being secured, if applicable, at the implantation site.

According to the invention, a coating refers to the application, at least in sections, of the components of the coating on the base body of the implant. In the case of a stent, the coating is preferably applied to the implant only abluminally. A layer thickness is preferably in the range of 1 nm to 100 μm, and particularly preferably 300 nm to 15 μm. The coating according to the invention can be applied directly to the implant surface, or additional intermediate layers can be provided; the base body of the implant may contain an inorganic base layer (e.g. sol-gel coatings) that improves the adhesion of the coating according to the invention. Additional layers can be applied to the coating according to the invention e.g. to simplify the introduction of the implant into the body. Methods for coating implants are known to a person skilled in the art (e.g. pipetting, rolling). To make the coating according to the invention, the auxiliary agent can first be applied to the entire surface, and then this coating can be structured in the sense of the invention. The sections of the coating in which the auxiliary agent was removed in the structuring process are then filled with the active agent. The structuring can take place e.g. by stamping, irradiation, or laser/temperature pressing.

According to a first, preferred embodiment, the individual subsections are designed such that the result is a pattern of alternating strips of the first and the second subsections. In particular, one width of the strips that form the first subsection of the coating is in the range of 1 to 30 μm. The pattern can be regular in particular. The stated dimension and pattern design has proven particularly effective for accelerating the adhesion behavior of a stent in the vascular wall.

According to a second, preferred embodiment, the individual subsections are designed such that the result is a pattern of islands of the first subsection enclosed by the second subsection. In particular, one width or one diameter of the islands that form the first subsection of the coating is in the range of 1 to 30 μm. The pattern can be regular in particular. The stated dimension and pattern design has proven particularly effective for accelerating the adhesion behavior of a stent in the vascular wall.

Preferably, a base body of the implant is composed of a biocorrodible material, in particular a biocorrodible magnesium alloy.

Within the scope of the invention, those materials are referred to as being biocorrodible that degrade/convert in a physiological environment, and therefore the part of the implant composed of the material is then no longer present or at least substantially no longer present.

In this context, a magnesium alloy is understood to be a metallic microstructure having magnesium as the main component. The main component is the alloy component that comprises the largest percentage by weight of the alloy. A percentage of the main component is preferably more than 50% by weight, in particular more than 70% by weight. The composition of the alloy should be selected such that the alloy is biocorrodible.

Artificial plasma, as has been previously described according to EN ISO 10993-15:2000 for biocorrosion assays (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l), is used as a testing medium to test the corrosion behavior of an alloy under consideration. To perform the test, a sample of the alloy to be investigated is stored in a closed sample container with a defined quantity of the test medium at 37° C. and pH 7.38. At time intervals defined according to the anticipated corrosion behavior, of a few hours up to multiple months, the samples are removed and examined in a known manner for traces of corrosion. The artificial plasma according to EN ISO 10993-15:2000 corresponds to a medium similar to blood and thus represents a possibility for reproducibly simulating a physiological environment within the scope of the invention.

Within the scope of the invention, implants are devices introduced into the body using a surgical procedure, and comprise fastening elements for bone, such as screws, plates, or nails, surgical suture material, intestinal clamps, vascular clips, prostheses in the area of hard and soft tissue, and anchoring elements for electrodes, in particular of pacemakers or defibrillators. The implant is composed entirely or in parts of the biocorrodible material. The implant is preferably a stent, The first subsection of the coating contains one or more active agents which are released after implantation. According to the invention, an active agent is a medicinal agent having a pharmaceutical effect, and which is used in the human body or animal body to cure, alleviate, prevent, or detect illness. Active agents include paclitaxel, sirolimus, and their derivatives in particular. In particular, active agents are advantageous that act on mammalian target of rapamycin (mTOR), and rat sarcoma (RAS) inhibitors, in particular those that prevent RAS adhesion.

Preferably, the auxiliary agent can be dissolved completely in vivo in fewer than 10 h, in particular 2 h. The auxiliary agent can consist of 80% or more by weight of a sugar or a sugar derivative. For example, mixtures of 6-O-α-D-Glucopyranosyl-D-sorbitol (1,6-GPS) and 6-O-α-D-Glucopyranosyl-D-mannitol dihydrate (1,1-GPM) can be used. Other possibilities include isomalt, lactose, cellulose powder, mannitol, calcium diphosphate, or sorbitol.

DETAILED DESCRIPTION

The invention is explained in greater detail in the following with reference to an embodiment and FIGS. 1A-1D. The figure series is a schematic depiction of a way to manufacture the coating according to the invention.

Figure 1A:
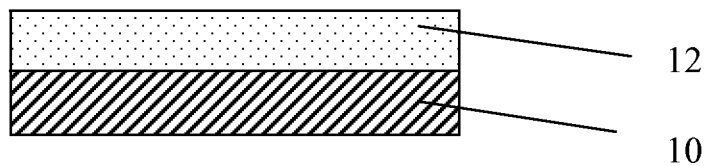
FIGS. 1A-D depict an overview of an exemplary method for manufacturing a coating for an implant and its state after implantation.
Figure 1B:
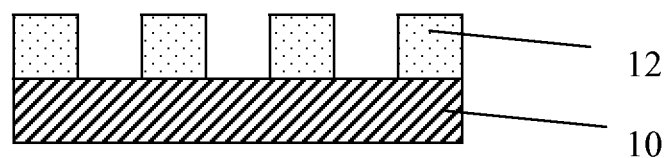
Figure 1C:
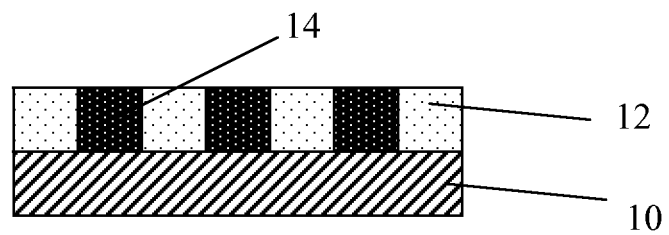
Figure 1D:
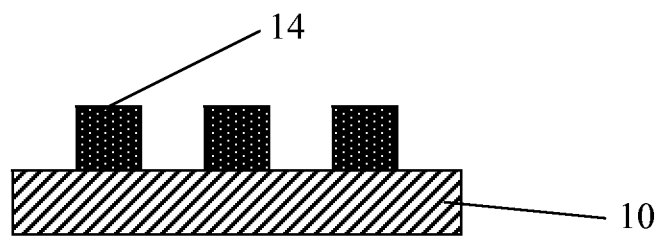

FIGS. 1A-C show, in a highly schematized illustration of substeps A to C, one way to manufacture the coating according to the invention, and shows the state after implantation, in FIG. 1D. In substep A, the base body of implant 10 is coated with auxiliary agent 12, thereby resulting in a closed surface. In substep B, grooves are formed in this surface e.g. by stamping; the grooves are filled with the active agent in substep C, thereby resulting in a closed coating overall. Auxiliary agent 12 is designed to dissolve quickly after implantation, thereby resulting in a structure after implantation that is similar to that shown in substep D in a highly schematicized manner.

Embodiment

A coating of the auxiliary agent is applied to a stent using an aerosol mist procedure. The auxiliary agent is a 1:1 mixture of 6-O-α-D-Glucopyranosyl-D-sorbitol (1,6-GPS) and 6-O-α-D-Glucopyranosyl-D-mannitol dihydrate (1,1-GPM) which is dissolved in water for the aerosol mist procedure. This auxiliary agent is available for galenical applications under the name GALENIQ oder Palatinit. It is easily structured under pressure and, unlike corn starch, dissolves easily in the bloodstream without complications. The layer thickness in this case is 200 nm to 5 μm, preferably 1 to 3 μm. Stamping is used to form grooves in the coating of auxiliary agent having a width of approximately 1-30 μm. Next, the grooves are filled with the active agent. The following are used for this purpose: paclitaxel or rapamycin in combination with an excipient from the group iopromide (SeQuent Please), FreePac (Invatec), butyryl-n-trihexyl-citrate (BTHC) or triethyl citrate. After implantation, the auxiliary agent dissolves rapidly and the layer of active agent remains.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implant comprising a base body and a coating which covers the base body, the coating comprising least two adjacent subsections; a first subsection containing at least one active agent, and a second subsection containing an auxiliary agent, wherein at least one of the subsections is a polymer free section, further wherein the first subsection fills grooves in the second subsection thereby remaining partially uncovered and the second subsection is configured to dissolve after implantation thereby increasing exposure of the first subsection to a surrounding medium.

2. The implant according to claim 1, wherein the individual subsections are designed such that the result is a pattern of alternating strips of the first and the second subsections.

3. The implant according to claim 2, wherein one width of the strips that form the first subsection of the coating is in the range of 1 to 30 μm.

4. The implant according to claim 2, wherein the pattern repeats.

5. The implant according to claim 1, wherein the individual subsections are designed such that the result is a pattern of islands of the first subsection enclosed by the second subsection.

6. The implant according to claim 5, wherein one width or one diameter of the islands that form the first subsection of the coating is in the range of 1 to 30 μm.

7. The implant according to claim 1, wherein the base body of the implant is composed of a biocorrodible material.

8. The implant according to claim 7, wherein the base body is composed of a biocorrodible magnesium alloy.

9. The implant according to claim 1, wherein the active agent is selected from the group consisting of paclitaxel, sirolimus, a derivative of sirolimus, and one or more RAS inhibitors.

10. The implant according to claim 1, wherein the auxiliary agent dissolves completely in vivo in fewer than 10 h.

11. The implant according to claim 10, wherein the auxiliary agent comprises 80% or more by weight of a sugar or a sugar derivative.

12. The implant according to claim 1, wherein the implant is a stent.

13. The implant according to claim 1, wherein the first subsection is the polymer free section.

14. The implant according to claim 1, wherein the second subsection is the polymer free section.

15. The implant according to claim 1, wherein both the first and second subsections are polymer free.

16. The implant according to claim 1, wherein both the first and second subsections form a closed coating preventing access to the base body.

* * * * *